Figure 1:
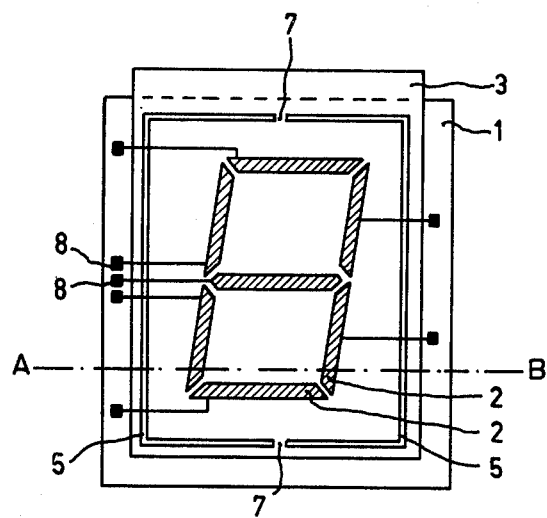

United States Patent [19]
van der Veen et al.

[11] 3,984,392

[45] Oct. 5, 1976

[54] LIQUID CRYSTALLINE AZOBENZENE COMPOUNDS

[75] Inventors: Jan van der Veen; Theodorus Cornelis Jozef Maria Hegge, both of Eindhoven, Netherlands

[73] Assignee: U.S. Philips Corporation, New York, N.Y.

[22] Filed: Dec. 9, 1974

[21] Appl. No.: 531,087

[30] Foreign Application Priority Data

Dec. 13, 1973 Netherlands .................... 7317074

[52] U.S. Cl. ................................. 260/206; 252/299
[51] Int. Cl.² ..................................... C07C 107/06
[58] Field of Search ............. 260/206; 252/408 LC, 252/299

[56] References Cited
UNITED STATES PATENTS 3,773,747  11/1973  Steinstrasser .................. 260/206 X
3,853,785  12/1974  Labes ........................... 252/408 LC

FOREIGN PATENTS OR APPLICATIONS 2,024,269  12/1971  Germany ........................ 252/299

*Primary Examiner*—Charles F. Warren
*Attorney, Agent, or Firm*—Frank R. Trifari; Norman N. Spain

[57] ABSTRACT

Novel nematic liquid crystalline azo-compounds have been found, which are anisotropic over a wide temperature range which includes room temperature.

The compounds are temperature, light and moisture proof. They exhibit no dynamic scattering. The compounds may be employed in E.S.R. and N.M.R. spectroscopy, and, as the case may be mixed with other nematic liquid crystalline compounds, in displays.

3 Claims, 2 Drawing Figures

LIQUID CRYSTALLINE AZOBENZENE COMPOUNDS

The invention relates to novel liquid crystalline compounds.

Many liquid crystalline compounds have too high a melting point or too small a liquid-crystalline temperature range for practical applications.

It is an object of the invention to provide nematic liquid crystalline compounds, which are liquid crystalline over a wide temperature range and which melt below room temperature.

It has been found that novel compounds of the formula

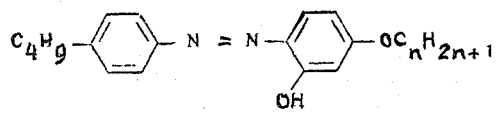

(1)

in which $n$ has the value 6 or 7, and mixtures of said compounds meet the object in view.

The compounds are resistant to the effects of temperature, light and hydrolysis. They exhibit no dynamic scattering. The compounds can be applied as solvents in E.S.R. and N.M.R.-spectrocopy. Furthermore, they may be employed in displays. If desired they may be mixed with other liquid crystalline compounds, for example nematic liquid crystalline compounds which exhibit dynamic scattering. Examples of nematic liquid crystalline compounds which may be mixed with the compounds according to the invention are the compounds described in French Pat. No. 1,537,000, the published Netherlands Pat. application No. 7,007,912, and the published German Pat. applications 1,928,242; 2,017,727 and 2,038,780.

The invention relates to novel compounds of the formula

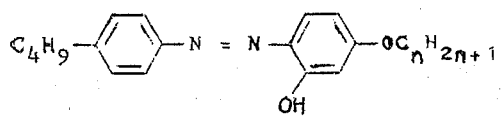

(1)

where $n = 6$ or 7, and to mixtures which contain at least one of said compounds.

It is to be noted that in Molecular Crystals and Liquid Crystals 11 187–189 (1970) o-hydroxy-p-methoxybenzyl-p-n.butylanilide is described as a nematic liquid crystalline compound. Said compound however, has a melting point of 44°C. It is true that the substance is liquid crystalline up to 64.5°C and below the melting point to 8°C, but the substance already crystallizes in a thin layer at 26°C.

The azo-compound which corresponds to said compound, p-n.butyl-o'-hydroxy-p'-methoxyazobenzene even appears to melt at a still higher temperature, 68°C, and to be liquid crystalline in undercooled condition only, to 60°C.

Hence it is the more surprising that the compounds of the formula 1 and mixtures formed therewith are liquid at room temperature and are liquid crystalline over a very wide range.

The surprising properties of the compounds found are illustrated by the table below

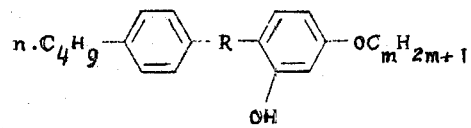

| R | $C_mH_{2m+1}$ | melting point °C | $T_c$°C | |
|---|---|---|---|---|
| N = C | $CH_3$ | 44 | 64.5 | |
| N = N | $CH_3$ | 68 | 60 | |
| N = N | $n.C_6H_{13}$ | 8* | 82 | I |
| N = N | $n.C_7H_{15}$ | 22–23 | 79 | II |
| 35.05 mol % I + 64.95 mol % II | | 9–15 | 75 | |
| 49.64 mol % I + 50.034 mol % II | | 8.5–13 | 75 | |
| 70.15 mol % I + 29.85 mol % II | | 0–2 | 75 | |

*A second crystal modification melts at 17°C.

The compounds of the formula 1 can be obtained in accordance with methods known per se.

For example the compounds may be prepared by reacting o, p-dihydroxy-p'-butylazobenzene or an alkali metal salt thereof with an alkylhalide of the formula 2

$$C_nH_{2n+1}X \qquad (2)$$

where $n$ is 6 or 7 and X represents an iodine or bromine atom. The reaction is preferably performed in a highly polar aprotic solvent, such as for example dimethylformamide, at temperatures between room temperature and the boiling point of the mixture.

The azobenzene compound which is the starting point of said reaction is obtained by reacting p-butylphenyl-diazonium-tetra-fluoroborate with resorcinol in acetone/water between 0° and 5°C.

The compounds according to the invention and mixtures of nematic liquid-crystalline compounds with at least one of the compounds according to the invention may be successfully employed in display cells. Hence, the invention also relates to a display cell provided with at least two electrodes and a nematic liquid crystalline material disposed therebetween, characterized in that the liquid crystalline material contains at least one or more of the compounds of the formula 1.

Figure 2:
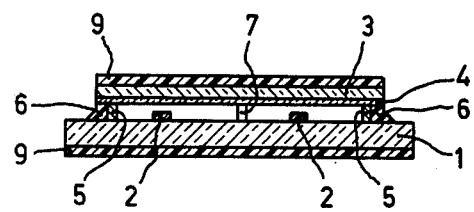

The invention will now be explained in more detail with reference to the drawing in which FIG. 1 shows a plan view of the display cell before the polarization filters were mounted, while FIG. 2 is a cross-section taken at the line A-B after the filters were mounted.

1a. To 0.1 mol of p-n.butylaniline in 40 ml of water 30 ml of concentrated HCl were added whilst stirring. Subsequently the reaction mixture was cooled at 0°C. To said mixture 0.1 mol of sodium nitrite, dissolved in water were added whilst stirring, so that the temperature of the reaction mixture remained between 0°C and 5°C. After adding the sodium nitrite solution stirring was continued for 15 minutes. Subsequently, 0.15 mol of ammoniumborofluoride dissolved in water, were added to said reaction mixture. The precipitated diazoniumborofluoride was filtered off and washed with cold water after being kept in the refrigerator for one hour. The diazoniumborofluoride was dissolved in a mixture of 100 ml of water and acetone (1 : 1). Subsequently 0.15 mol of resorcinol, solved in 120 ml of water, were added. Said solution was kept in the refrigerator for 16 hours and subsequently poured into 500 ml of water. The resultant precipitate of 4-n-butyl-2',4'-dihydroxyazobenzene was filtered off.

b. 0.10 mol of 4-n.butyl-2',4'-dihydroxyazobenzene were dissolved in 200 ml of methanol and 0.1 mol of potassium hydroxide were added. The mixture was heated until the potassium hydroxide had fully dissolved. Subsequently, the methanol was removed by vacuum. To the residue of 50 ml of absolute ethanol and 50 ml of benzene were added. The solvents were extracted in vacuum. Said procedure was repeated twice. Finally, the residue was taken up in petroleum ether and the precipitate was filtered off.

c. 0.05 mol of the potassium salt of 4-n.butyl-2',4'-dihydroxyazobenzene were dissolved in 300 ml of dimethylformamide. To this 0.05 mol of n.hexyliodide were added while stirring and the mixture was subsequently heated to 110°C. After the mixture had been kept at this temperature for 30 minutes, 0.025 mol of n.hexyliodide were added and the mixture was stored for another 45 minutes at 110°C. Finally, the reaction mixture was poored out in water and shaked with petroleum ether. The petroleum ether extract was dried on a molecular sieve with a pore size of 4 A°. The petroleum ether was removed in vacuo. The oily residue was recrystallized twice from abs. ethanol. Melting point 8°C.

2. In a similar way as in example 1c 4-n.butyl-2'-hydroxy-4'-n.heptyloxyazobenzene was obtained starting from the potassium salt of 4-n.butyl-2',4'-dihydroxyazobenzene and n.heptyliodide. Melting point 22°-23°C.

3. A glass plate measuring 60 × 65 × 2 mm (1 in FIGS. 1 and 2) which was provided with an 8-shaped pattern of indium oxide (thickness of layer 0.1 nm) consisting of 7 segments 2, and a second glass plate 3 measuring 50×60×1 mm which was covered with a tin oxide layer 4 having a thickness of 0.1 nm, were each rubbed in one direction, with a piece of lens paper at the oxide-coated side, glass plate being rubbed in the longitudinal direction and the glass plate 3 being rubbed in the transverse direction.

On glass plate 1 two 20 nm thick polythene strips were placed, onto which glass plate 3 was placed. The glass plates were connected with an epoxy glue filling, openings 7 being left. The space between the glass plates was then filled with p-n.butyl-o'-hydroxy-p'-n.hexyloxyazobenzene. The openings 7 were closed with epoxy glue.

Current supply leads were fitted to the connection points 8 which consisted of indium oxide, as well as on the part of glass plate 3 which extended beyond the glass plate 1. The underside of glass plate 1 and the upper side of glass plate 3 were provided with polarising filters. The direction of polarization of the two filters was parallel to the direction in which plate 1 had been rubbed with lens paper. The display cell thus obtained when viewed through showed a dark image field.

At the oxide-coated surface of the glass plates, the molecules of the nematic liquid crystalline substance are disposed parallel to the surface and in the direction of rubbing. Since said directions are perpendicular to each other, the liquid crystalline layer has a twisted structure.

Across the glass plate 3 and the segments on plate 1 an alternating voltage of 6 V, 50 Hz was applied. This yielded a bright 8-shaped image. At the location of the segments 2 the molecules are oriented perpendicular to the surface of the glass plates, so that the cell becomes locally transparent.

FIG. 1 shows a plan view of the display cell before the polarisation filters were mounted, whilst FIG. 2 is a cross-section taken at the line A-B after the filters were mounted.

What is claimed is:

1. A compound of the formula 1

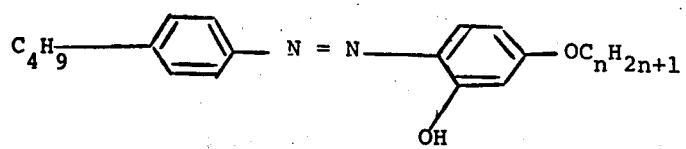

where $n$ is 6 or 7.

2. 4-n.butyl-2'-hydroxy-4'-n.hexyloxyazobenzene.
3. 4-n.butyl-2'-hydroxy-4'-n.heptyloxyazobenzene.

* * * * *